(12) United States Patent
Meunier et al.

(10) Patent No.: US 11,058,575 B2
(45) Date of Patent: Jul. 13, 2021

(54) METHOD AND SYSTEM FOR DELIVERING EXOGENOUS BIOMOLECULES INTO THE EYE AND METHOD FOR FORMING PORES INTO TARGET CELLS OF AN EYE

(71) Applicant: ECOLE POLYTECHNIQUE, Montréal (CA)

(72) Inventors: Michel Meunier, Pierrefonds (CA); Ariel Wilson, Montreal (CA); Éric Bergeron, Saint-Jean-sur-Richelieu (CA); Javier Mazzaferri, Montreal (CA); Santiago Costantino, Montreal (CA); Przemyslaw Sapieha, Beaconsfield (CA)

(73) Assignee: ÉCOLE POLYTECHNIQUE, Montréal (CA)

( * ) Notice: Subject to any disclaimer, the term of this patent is extended or adjusted under 35 U.S.C. 154(b) by 330 days.

(21) Appl. No.: 16/168,982

(22) Filed: Oct. 24, 2018

(65) Prior Publication Data

US 2019/0117451 A1 Apr. 25, 2019

Related U.S. Application Data

(60) Provisional application No. 62/576,973, filed on Oct. 25, 2017.

(51) Int. Cl.
| | |
|---|---|
| *A61F 9/008* | (2006.01) |
| *A61F 9/00* | (2006.01) |
| *C12N 15/82* | (2006.01) |
| *A61K 49/00* | (2006.01) |
| *A61B 3/13* | (2006.01) |
| *A61K 47/60* | (2017.01) |

(52) U.S. Cl.
CPC ............ *A61F 9/0008* (2013.01); *A61F 9/008* (2013.01); *A61F 9/00825* (2013.01); *A61K 49/0065* (2013.01); *C12N 15/8207* (2013.01); *A61B 3/13* (2013.01); *A61F 2009/00863* (2013.01); *A61K 47/60* (2017.08)

(58) Field of Classification Search
CPC .................................................... A61F 9/0008
See application file for complete search history.

(56) References Cited

U.S. PATENT DOCUMENTS

| | | | |
|---|---|---|---|
| 6,627,421 B1 | 9/2003 | Unger et al. | |
| 7,834,331 B2 | 11/2010 | Ben-Yakar et al. | |
| 8,435,791 B2 | 5/2013 | Galun et al. | |
| 8,815,212 B2 | 8/2014 | Emelianov et al. | |
| 9,550,069 B1 | 1/2017 | Elezzabi | |
| 2005/0203495 A1 | 9/2005 | Malak | |
| 2006/0075514 A1 | 4/2006 | Flotte et al. | |
| 2006/0141624 A1 | 6/2006 | Koenig et al. | |
| 2013/0052725 A1 | 2/2013 | Yazdanfar et al. | |
| 2013/0164828 A1 | 6/2013 | Dholakia et al. | |
| 2013/0230167 A1 | 9/2013 | Bauchot et al. | |
| 2014/0350452 A1 | 11/2014 | Millenbaugh et al. | |
| 2015/0343090 A1 | 12/2015 | Zasadzinski et al. | |

FOREIGN PATENT DOCUMENTS

| | | |
|---|---|---|
| DE | 10223921 A1 | 12/2003 |
| EP | 1818399 A1 | 1/2001 |
| EP | 2556149 B1 | 4/2011 |
| JP | 2010235453 A | 10/2010 |
| WO | 2006037236 A1 | 4/2006 |
| WO | 2007099312 A1 | 9/2007 |
| WO | 2009140701 A2 | 11/2009 |
| WO | 2011091283 A1 | 7/2011 |
| WO | 2011159606 A1 | 12/2011 |
| WO | 2013030245 A1 | 3/2013 |
| WO | 2013148158 A1 | 10/2013 |
| WO | 2015088042 A1 | 6/2015 |
| WO | 2016042162 A1 | 3/2016 |
| WO | 2016042163 A2 | 3/2016 |

OTHER PUBLICATIONS

Lajunen et al. (Journal of Controlled Release 203 (2015) 85-98) (Year: 2015).*
Jain et al. (J. Phys. Chem. B2006, 110, 7238-7248) (Year: 2006).*
Off-resonance plasmonic enhanced femtosecond laser optoporation and transfection of cancer cells, Judith Baumgart; Article in Biomaterials—Dec. 2011, from the Internet https://www.researchgate.net/publication/51896208.
Pan-Retinal Photocoagulation; From the Internet http://www.pgheyes.com/resources/procedures/pan-retinal-photocoagulation.
Spectral and temporal pulsed laser plasmonics enhanced (STAPLE) process; M. Meunier, R. Lachaine and E. Boulais, 2012-2013.

* cited by examiner

*Primary Examiner* — Scott Long
(74) *Attorney, Agent, or Firm* — Norton Rose Fulbright Canada LLP; Reno Lessard

(57) ABSTRACT

There is described a method for delivering exogenous biomolecules into an eye. The method generally has the steps of injecting, into a region of the eye, a mixture having a plurality of exogenous biomolecules and a plurality of plasmonic structures, the plasmonic structures having a plasmonic resonance wavelength, the plasmonic structures adjoining membranes of target cells in said region due to said injecting; and irradiating said region of said eye with a laser beam having a wavelength being offset to said plasmonic resonance wavelength, said irradiating causing the plasmonic structures to form pores in said membranes of said target cells, allowing at least some of the exogenous biomolecules to be delivered into the target cells via said pores.

19 Claims, 7 Drawing Sheets

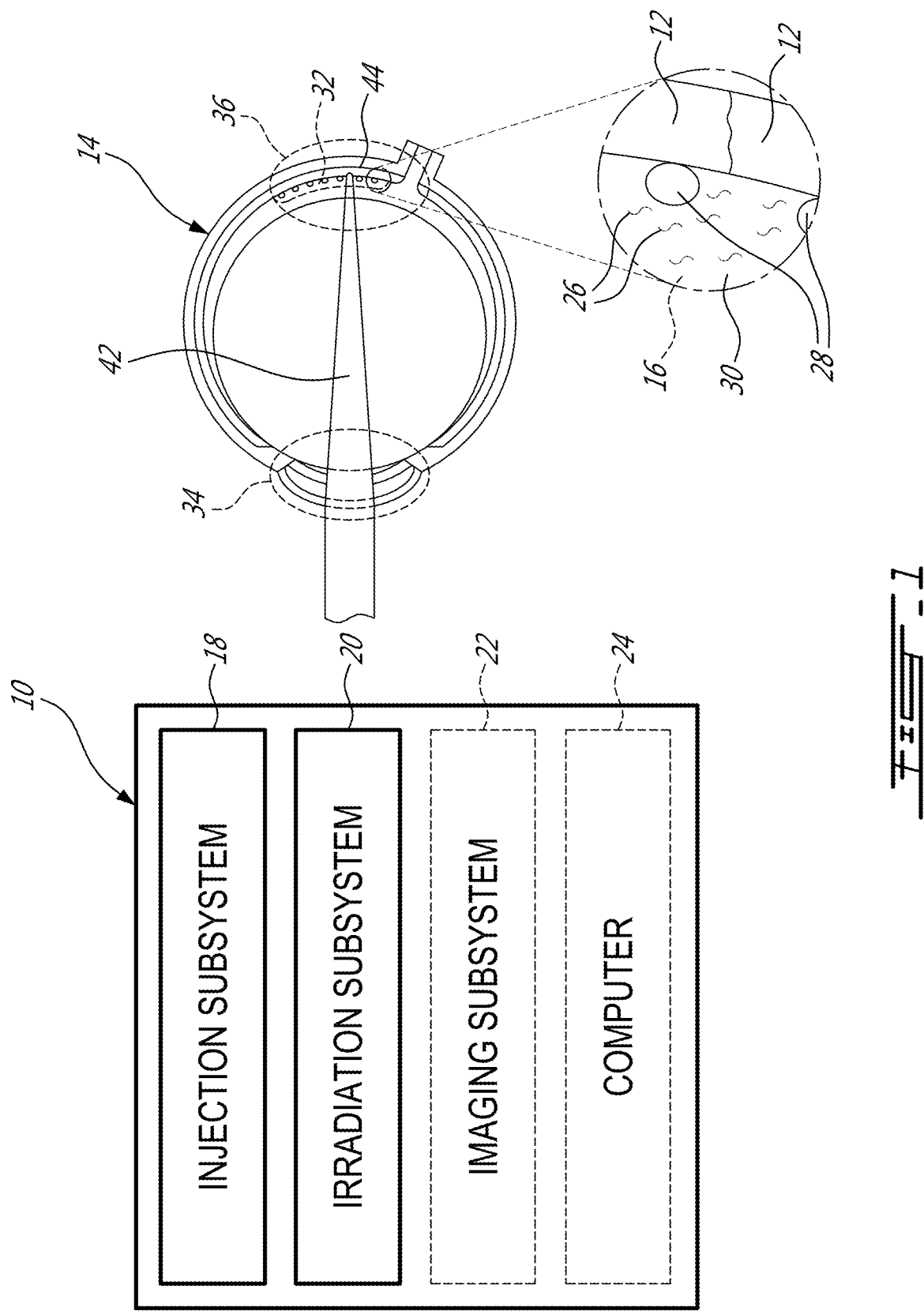

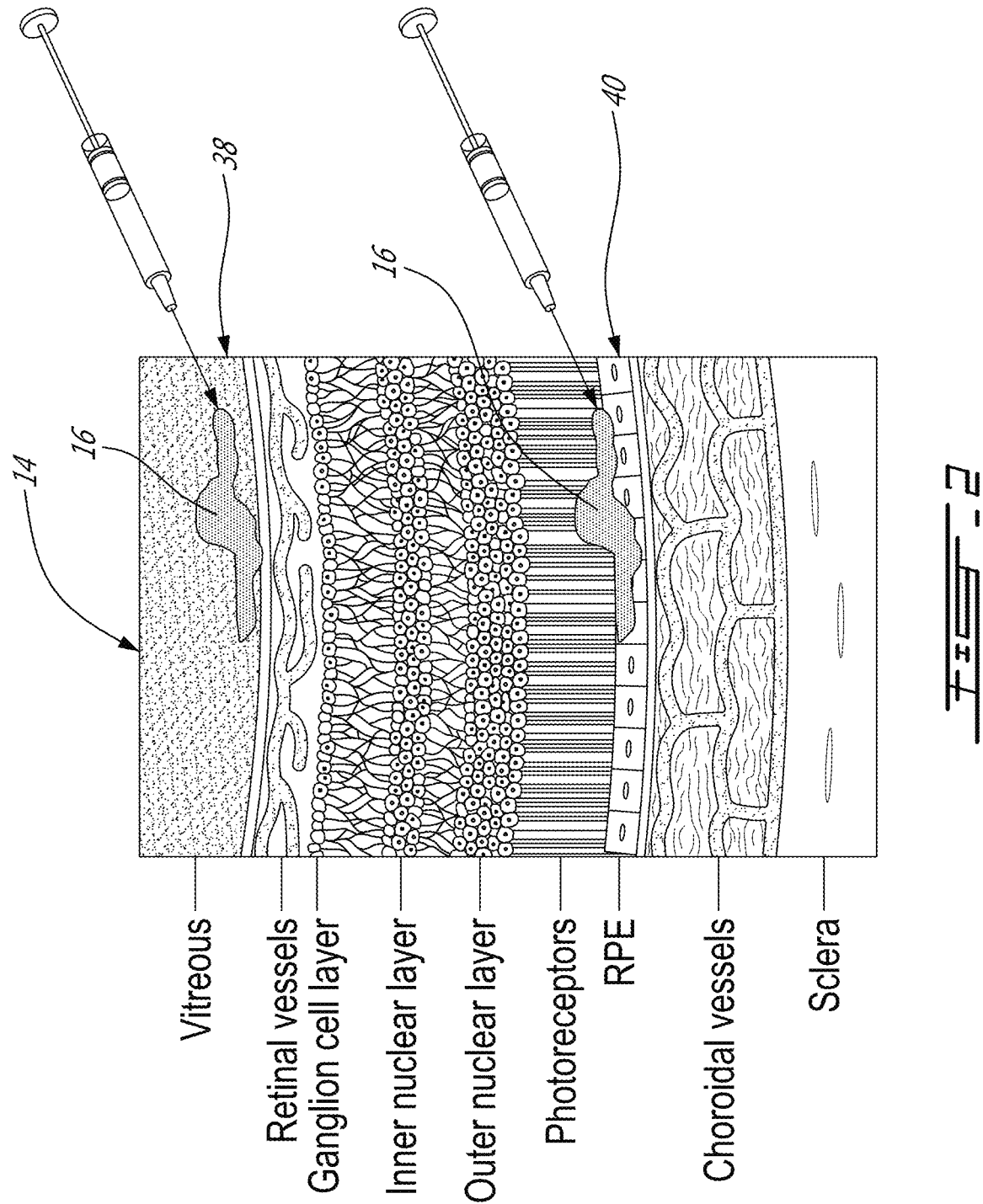

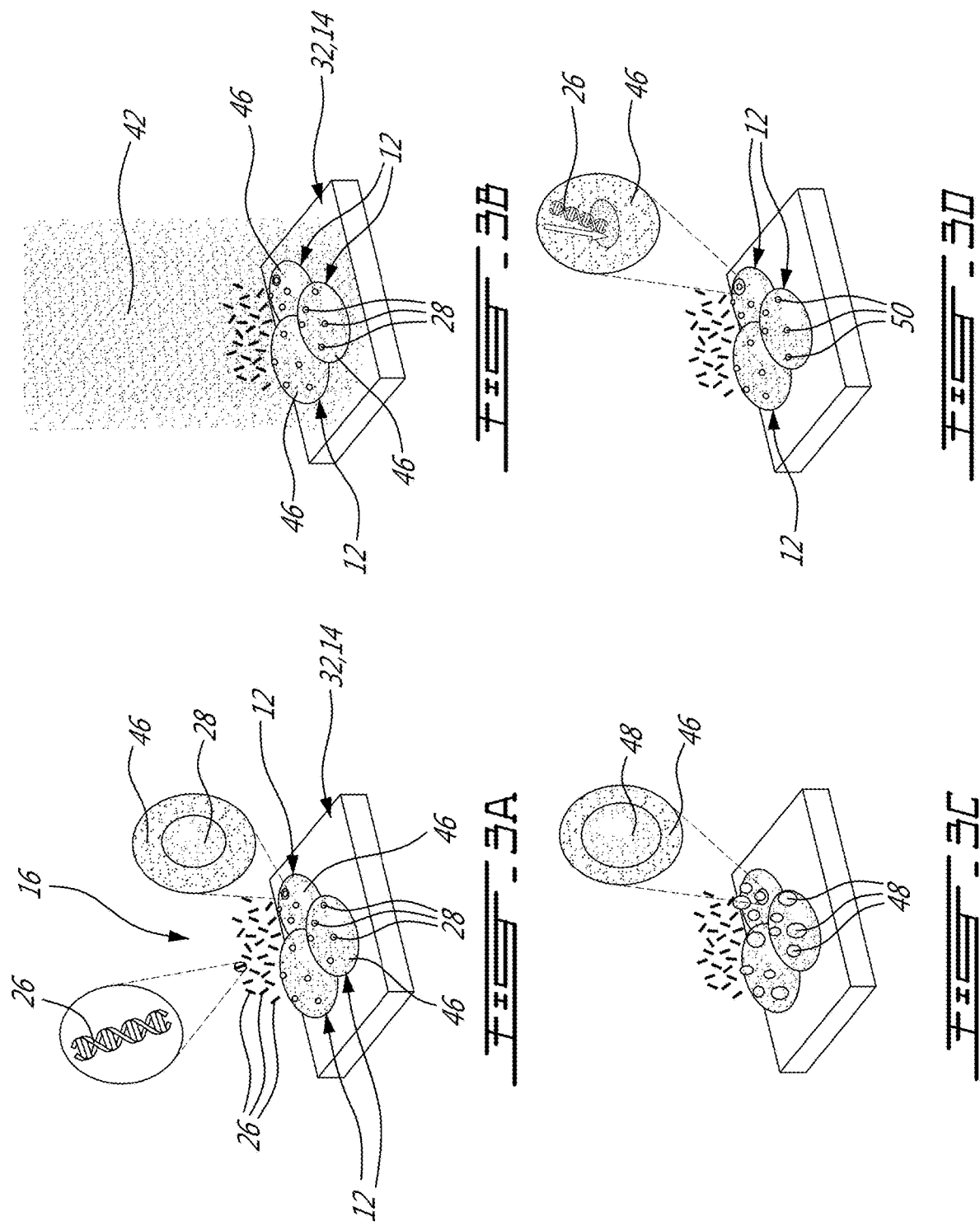

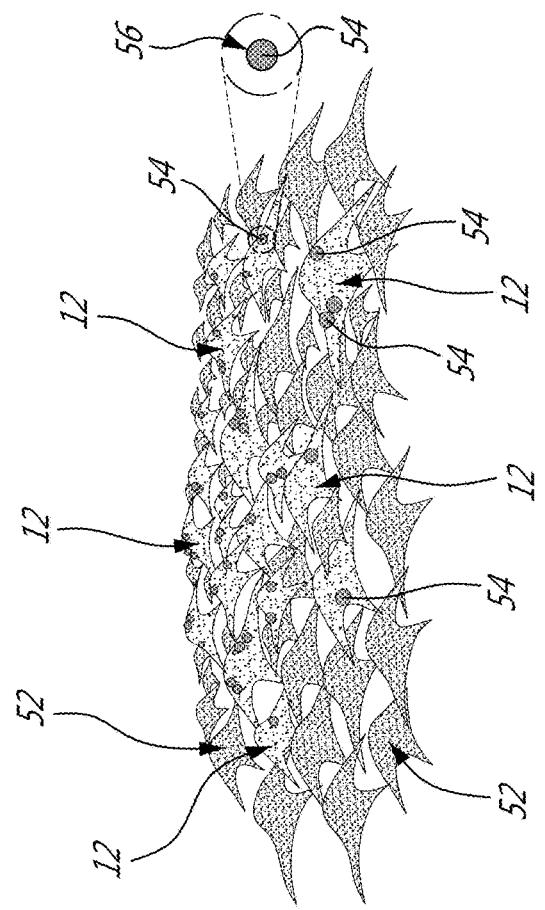
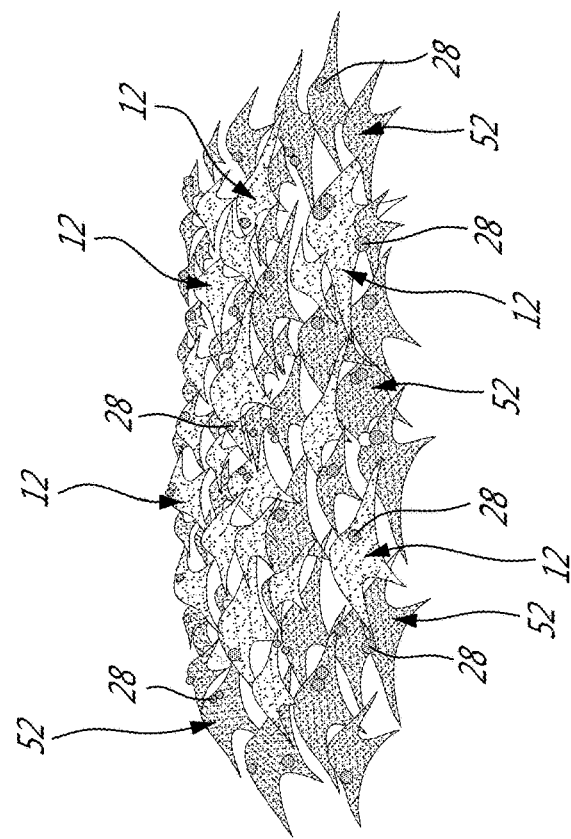

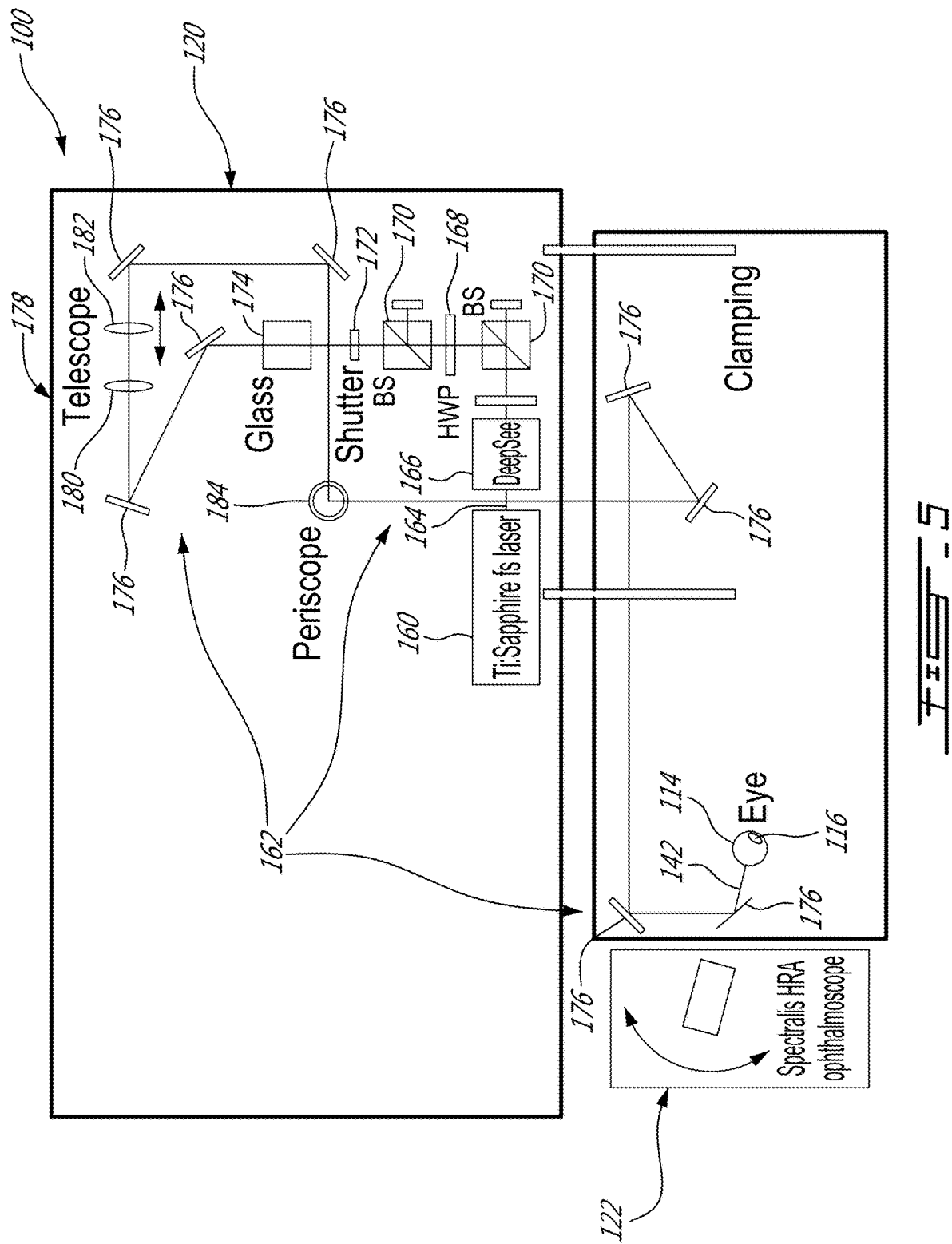

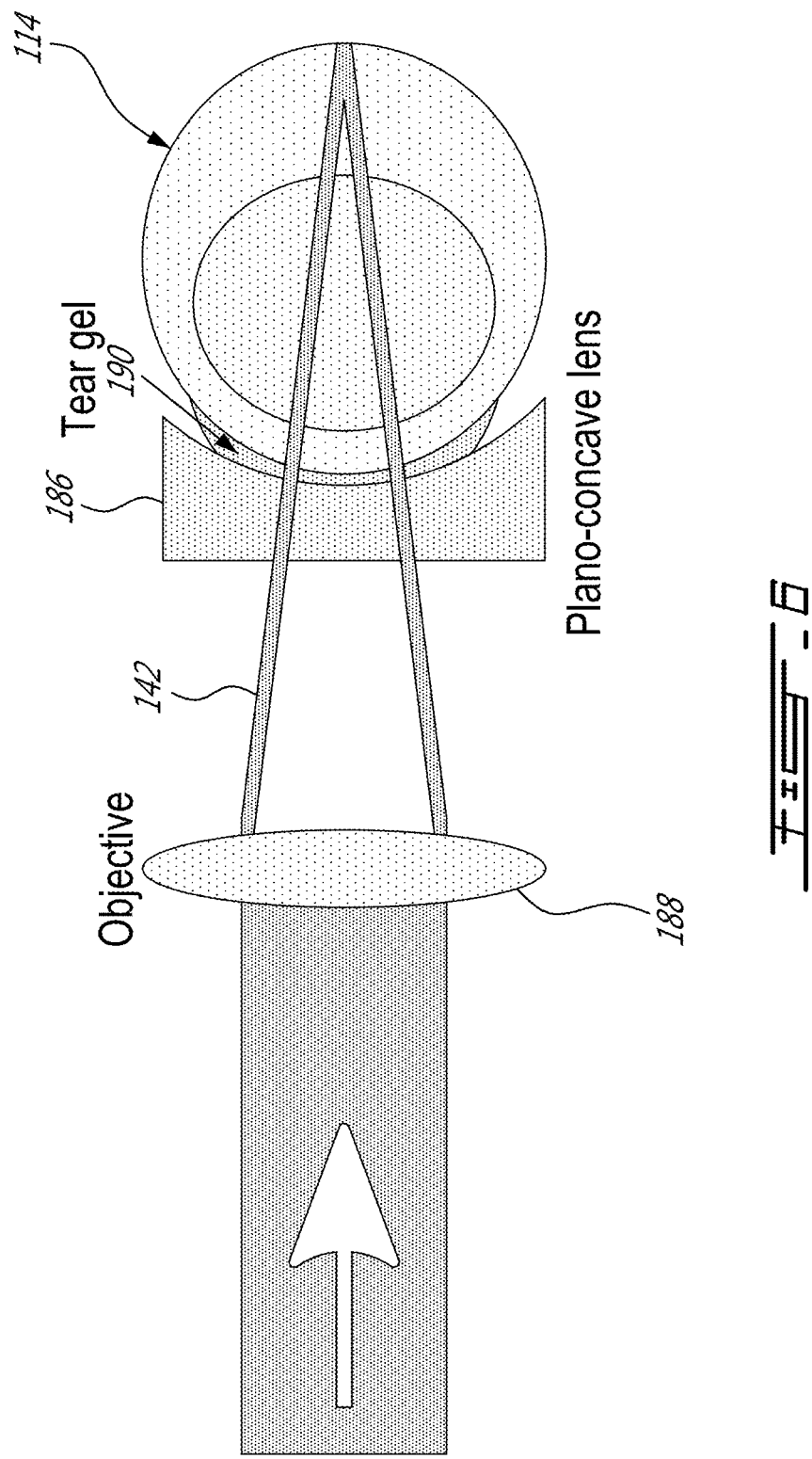

METHOD AND SYSTEM FOR DELIVERING EXOGENOUS BIOMOLECULES INTO THE EYE AND METHOD FOR FORMING PORES INTO TARGET CELLS OF AN EYE

FIELD

The improvements generally relate to the field of delivering exogenous biomolecules into target cells, and more specifically relate to the field of in vivo delivering exogenous biomolecules into target cells of a human eye or other living organisms' eyes.

BACKGROUND

The human eye, or other types of eyes, generally has a cornea, i.e., a transparent layer at the front of the eye, and a retina, i.e., nerve cells in the back of the eye.

Ocular diseases affecting the retina or the cornea are leading causes of vision loss and affect millions of individuals worldwide. For instance, one example of an ocular disease of the retina includes age-related macular degeneration (AMD), which can cause severe visual impairments due to the dysfunction of photoreceptor cells, retinal pigment epithelium (RPE) cells or choroidal neovascularization (CNV) in the macula. Glaucoma, another leading cause of blindness, affects retinal ganglion cells and causes their degeneration. Also, examples of ocular diseases of the cornea include corneal endothelial diseases, which can lead to endothelial cell decompensation and/or corneal blindness.

Treatments for such ocular diseases exist. For instance, U.S. Pat. No. 9,550,069 B1, to Elezzabi, describes a treatment for irradiating extracellular macular deposits through the cornea of an eye utilizing laser pulses. In this treatment, by focusing the laser pulses at a depth targeting extracellular macular deposits, the irradiating laser pulses are configured to ionize, remove, deplete, denature, and destroy the extracellular macular deposits. Although existing ocular disease treatments are satisfactory to a certain degree, there remains room for improvement.

SUMMARY

Given the postmitotic nature of the retina, destroying cells of the eye may be far from optimal for treating several ocular diseases. Alternative options to such treatments include exogenous biomolecules delivery methods by which exogenous biomolecules, such as genes, are delivered to a cell to treat it. Such methods have been found to limit the amount of biological damage and to provide satisfactory recovery times. However, delivering exogenous biomolecules into cells of the eye to treat them can be challenging.

In one aspect, there is provided a method for delivering exogenous biomolecules into the eye. The method involves the injection of exogenous biomolecules and plasmonic particles into a target region of the eye and the irradiation of the previously injected plasmonic particles, through the eye, which can lead to the introduction of the previously injected exogenous biomolecules into the cells of the target region.

In accordance with an aspect, there is provided a method for delivering exogenous biomolecules into an eye, the method comprising the steps of: injecting, into a region of the eye, a mixture having a plurality of exogenous biomolecules and a plurality of plasmonic structures, the plasmonic structures having a plasmonic resonance wavelength, the plasmonic structures adjoining membranes of target cells in said region due to said injecting; and irradiating said region of said eye with a laser beam having a wavelength being offset to said plasmonic resonance wavelength, said irradiating causing the plasmonic structures to form pores in said membranes of said target cells, allowing at least some of the exogenous biomolecules to be delivered into the target cells via said pores.

In accordance with another aspect, there is provided a method for delivering exogenous biomolecules into an eye, the method comprising: irradiating, with a laser beam, a region of the eye having an injectable mixture in said region of said eye, the injectable mixture having a plurality of exogenous biomolecules and a plurality of plasmonic structures adjoining membranes of target cells in said region, the laser beam having a wavelength being offset to a plasmonic resonance wavelength of the plurality of plasmonic structures, said irradiating causing the plasmonic structures to form pores in said membranes of said target cells, allowing at least some of the exogenous biomolecules to be delivered into the target cells via said pores.

In accordance with another aspect, there is provided a method for forming pores into target cells of an eye, the method comprising: irradiating, with a laser beam, a region of the eye having an injectable colloidal suspension in said region of said eye, the injectable colloidal suspension having a plurality of plasmonic structures adjoining membranes of said target cells in said region, the laser beam having a wavelength being offset to a plasmonic resonance wavelength of the plurality of plasmonic structures, said irradiating causing the plasmonic structures to form pores in said membranes of said target cells.

In accordance with another aspect, there is provided a system for forming pores into target cells of an eye, the system comprising: a mixture having a plurality of plasmonic structures and being injectable into a region of said eye in a manner resulting in the plasmonic structures adjoining membranes of said target cells of said eye, the plasmonic structures having a plasmonic resonance wavelength; and an irradiation subsystem configured for irradiating said region of said eye with a laser beam having a wavelength being offset to said plasmonic resonance wavelength, said irradiating causing the plasmonic structures to form pores in said membranes of said target cells.

In accordance with another aspect, there is provided a use of an injectable mixture for delivering exogenous biomolecules into an eye, the injectable mixture having a plurality of exogenous biomolecules and a plurality of plasmonic structures, wherein pores are formed in cells of the eye when the plurality of plasmonic structures are irradiated with a laser beam, the laser beam having a wavelength being offset to a plasmonic resonance wavelength of the plasmonic structures.

In accordance with another aspect, there is provided a use of an injectable colloidal suspension to form pores into targeted cells of an eye, wherein said injectable colloidal suspension having a plurality of plasmonic structures, wherein said pores are formed in said targeted cells when the plasmonic structures are irradiated having a wavelength being offset to a plasmonic resonance wavelength of the plurality of plasmonic structures.

In accordance with another aspect, there is provided a method for delivering exogenous biomolecules into an eye, the method comprising the steps of: injecting, into a region of the eye, a mixture having a plurality of exogenous biomolecules and a plurality of plasmonic structures, the plasmonic structures having a plasmonic resonance wavelength, the plasmonic structures adjoining membranes of target cells in said region due to said injecting; and irradiating said region of said eye with a laser beam, said irradiating causing the plasmonic structures to form pores in said membranes of said target cells, allowing at least some of the exogenous biomolecules to be delivered into the target cells via said pores.

It will be understood that the various functions of a computer or of a controller can be performed by hardware or by a combination of both hardware and software. For example, hardware can include logic gates included as part of a silicon chip of a processor. Software can be in the form of data such as computer-readable instructions stored in the memory system. With respect to a computer, a controller, a processing unit, or a processor chip, the expression "configured to" relates to the presence of hardware or a combination of hardware and software, which is operable to perform the associated functions.

It will be understood that in this disclosure the expression "laser beam having a wavelength" should be construed broadly so as to encompass situations where the laser beam has optical power at least within a spectral band associated to said wavelength.

Many further features and combinations thereof concerning the present improvements will appear to those skilled in the art following a reading of the instant disclosure.

DESCRIPTION OF THE FIGURES

In the figures,

FIG. 1 is a schematic view of a system for delivering exogenous biomolecules into a human eye, in accordance with an embodiment;

FIG. 2 is a sectional view of a portion of the human eye of FIG. 1, showing different types of injections, in accordance with an embodiment;

FIG. 3A is a schematic and oblique view of target cells of the human eye, shown with plasmonic structures adjoining membranes of target cells;

FIG. 3B is a schematic and oblique view of the target cells of FIG. 3A, showing a laser beam irradiating the plasmonic structures of FIG. 3A;

FIG. 3C is a schematic and oblique view of the target cells of FIG. 3A, showing bubbles around the previously irradiated plasmonic structures of FIG. 3B;

FIG. 3D is a schematic and oblique view of the target cells of FIG. 3A, showing pores at the locations of the bubbles of FIG. 3C;

FIG. 4A is a schematic view of target cells and non-target cells, showing plasmonic structures adjoining membranes of the target cells and membranes of the non-target cells, in accordance with an embodiment;

FIG. 4B is a schematic view of target cells and non-target cells, showing functionalized plasmonic structures adjoining membranes of the target cells only, in accordance with an embodiment;

FIG. 5 is an example of a system for delivering exogenous biomolecules into a rodent eye, shown with an imaging subsystem, in accordance with an embodiment;

FIG. 6 is a sectional view of the rodent eye of FIG. 5, showing an optical assembly focusing a laser beam onto a retina of the rodent eye, in accordance with an embodiment;

DETAILED DESCRIPTION

Figure 7A:
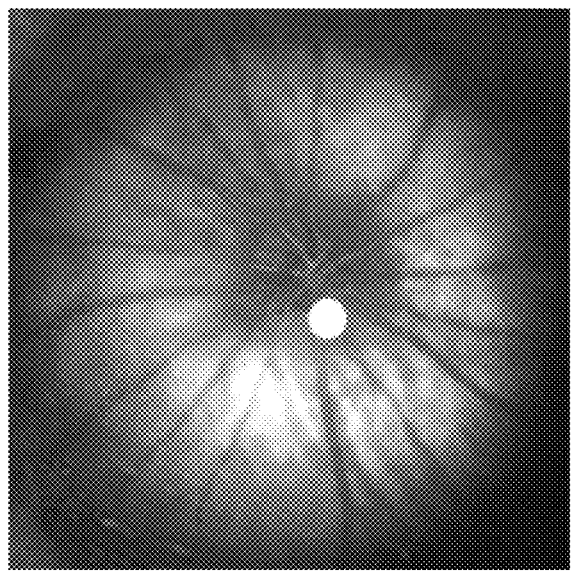
FIG. 7A is an image showing an ocular fundus ophthalmoscope visualization of a rodent eye, taken in vivo.

FIG. 1 shows a system 10 for delivering biomolecules into a target cell 12 of a human eye 14 or of any other eye. As depicted in this example, the system 10 has a mixture 16, an injection subsystem 18, an irradiation subsystem 20, an imaging subsystem 22 and a computer 24.

In this specific embodiment, the mixture 16 has exogenous biomolecules 26 and plasmonic structures 28. More specifically, the mixture 16 can be a mixture including a substance 30 into which the exogenous biomolecules 26 are dissolved and into which the plasmonic structures 28 are dispersed. In some embodiments, the mixture 16 can have a concentration of plasmonic structures 28, which is in the order of the ng/mL and up to the g/m L.

The exogenous biomolecules 26 are chosen to treat one or more ocular diseases of the target cell 12 into which they are to be delivered. For instance, the exogenous biomolecules 26 can be provided in the form of dyes, drugs, and transgene, i.e., a gene or genetic material that has been transferred naturally or by any of a number of genetic engineering techniques from one organism to another (e.g., DNA, siRNA). As it can be understood, the delivery of the exogenous biomolecules 26 has the potential to change a phenotype of the target cell 12 into which it is delivered, which may lead to correcting a genetic anomaly of that target cell 12, and thus eventually treating the ocular disease associated to the genetic anomaly. The composition and concentration of the exogenous biomolecules 26 in the mixture 16 can be determined on a case by case basis, allowing a treatment customized to the ocular disease(s) of the human eye 14.

The plasmonic structures 28 have one or more plasmonic resonance wavelengths $\lambda p$. As it will be understood, the plasmonic structures 28 are particles whose electron density can couple with laser beams of wavelengths that are far larger than the size of the plasmonic structure 28 due to the nature of the dielectric-metal interface between the medium and the plasmonic structure 28. Accordingly, the plasmonic structures 28 can absorb optical power of a laser beam more or less depending on its wavelength, and how the wavelength of the laser beam compares to the plasmonic resonance wavelength $\lambda p$. The composition, the geometry, the size, the concentration, and the functionalization are exemplary parameters of the plasmonic structures 28 that can vary from one embodiment to another.

The injector subsystem 18 is configured for injecting the mixture 16 into a region 32 of the human eye 14. In this specific example, the injector subsystem 18 is robotized in the sense that the injector subsystem 18 can inject the mixture 16 where desired in the human eye 14 without requiring manipulation of a syringe by a user. For instance, the injector subsystem 18 can include a robot arm having one end fixedly mounted relative to the floor or ceiling and another end having a syringe tool. The syringe tool can have a syringe containing the mixture 16. Accordingly, the robot arm can be manipulated, based on instructions received from the computer 24, to inject the mixture 16 where desired in the human eye 14 using the syringe tool at the end of the robot arm. Other embodiments of the injection subsystem 18 can also be used.

In some embodiments, the mixture 16 can be injected in a corneal region 34 of the human eye 14, and more specifically, in an intracameral region of the human eye 14. Alternately, or in addition, the mixture 16 can be injected in a retinal region 36 of the human eye 14. For instance, as shown in FIG. 2, the mixture 16 can be injected in an intravitreal region 38 of the human eye 14 and/or injected in a subretinal region 40 of the human eye 14.

Referring back to FIG. 1, the irradiation subsystem 20 is configured for irradiating the region 32 of the human eye 14 with a laser beam 42. The laser beam 42 has a wavelength $\lambda$, which is offset to the plasmonic resonance wavelength $\lambda p$ of the plasmonic structures 28. The offset can vary from one embodiment to another. However, in one specific example, a plasmonic resonance wavelength $\lambda p$ of 520 nm and a laser beam having a wavelength of 800 nm have been found satisfactory. In one other example, a plasmonic resonance wavelength $\lambda p$ of 750 nm and a laser beam having a wavelength of 800 nm could yield satisfactory results as well. Lower offset values could also be envisaged, depending on the circumstances. The irradiation subsystem 20 can include optical components used to direct and focus the laser beam 42 onto the region 32 of the human eye 14, as will be described below with reference to FIG. 5.

It can be appreciated that parameters of the laser beam 42 as controlled by the irradiation subsystem 20 can vary from one embodiment to another. For instance, the laser beam 42 can be a continuous-wave (CW) laser beam or a pulsed laser beam, depending on the embodiment. Examples of such parameters include wavelength of the laser beam 42, scanning speed of a focal point 44 of the laser beam 42, pattern of the scanning, fluence (energy per area), size of the focal point 44, irradiation time, optical power of the laser beam 42, pulse width of the pulsed laser beam, and pulse repetition rate (which can be fixed or adjustable). Indeed, in some embodiments, the laser beam 42 is a laser beam including laser pulses having time durations in the nanosecond range (~$10^{-9}$ s), in the picosecond range (~$10^{-12}$ s) or in the femtosecond range (~$10^{-15}$ s). In some embodiments, the wavelength $\lambda$ of the laser beam 42 is chosen to be within an optically transparent window of the human eye 14, i.e., in the near-infrared (NIR) region of the electromagnetic spectrum. As such, the wavelength $\lambda$ of the laser beam 42 can be 800 nm, 1064 nm, and any other suitable wavelength, depending on the irradiation subsystem 20 and on the plasmonic resonance wavelength $\lambda p$ of the plasmonic structures 28. In some embodiments, irradiating in the optically transparent window of an eye can reduce side effects due to the irradiation.

In this specific example, the imaging subsystem 22 is provided to image the region 32 of the human eye 14 under treatment. An example of such imaging subsystem can include the conventional Heidelberg Spectralis HRA ophthalmoscope. However, other types of imaging subsystems and ophthalmoscopes can be used.

Accordingly, it is contemplated that the computer 24 can be used to receive and process image data (e.g., 2D image data, 3D image data) representative of the human eye 14, or the region 32 thereof, from the imaging subsystem 22. As can be understood, the computer 24 can be used to send instructions concerning the injection of the mixture 16 at the specific region 32 of the human eye 14 based on the image data received and processed from the imaging subsystem 22. Moreover, it is also envisaged that the computer 24 can be used to send instructions concerning the irradiation of the laser beam 42 at the specific region 32 of the human eye 14 based on the image data received and processed from the imaging subsystem 22. Therefore, in this example, the injection and the irradiation can be performed in an automated manner to avoid mishandling and reduce the duration of the intervention.

FIG. 3A depicts that, after the injection of the mixture 16, one or more of the plasmonic structures 28 adjoin membranes 46 of the target cells 12 due to the injection of the mixture 26 in the region 32 of the human eye 14. For instance, a plasmonic structure 28 can be in contact with the membranes 46 of the target cells 12 or in close proximity with a membrane 46 of a target cell 12. It will be understood that the plasmonic structures 28 can adjoin the membranes 46 of the target cells 12 as early as during the injection of the mixture 16, or after the injection of the mixture 16. As depicted, some exogenous biomolecules 26 are in the vicinity of the target cells 12.

In some embodiments, an incubation period of time $\Delta t$ can be waited after the injection of the mixture 16, to allow the exogenous biomolecules 26 and/or the plasmonic structures 28 sufficient time to deposit or to travel towards the membranes 46 of the target cells 12. The incubation period of time $\Delta t$ can range, for example, between 0 and 3 hours, depending on the embodiment. However, it can be understood that the period of time $\Delta t$ can be determined according to the ocular disease to be treated and/or as a function of the region 32 of the human eye 14 to be treated. The incubation period of time $\Delta t$ can thus differ from one embodiment to another.

FIG. 3B shows the laser beam 42 irradiating the region 32 of the human eye 14, and more specifically, irradiating the plasmonic structures 28 adjoining the membranes 46 of the target cells 12. As can be understood, when irradiated with the laser beam 42 having a wavelength $\lambda$ which is offset to the plasmonic resonance wavelength $\lambda p$ of the plasmonic structures 28, i.e., when $\lambda \neq \lambda p$, the plasmonic structures 28 can lead to the absorption of a portion of the optical power of the laser beam 42 due to the near field effect around the nanostructure, which may cause heating of the surrounding medium around the plasmonic structures 28, and then formation of pores, while avoiding damaging surrounding cells.

FIG. 3C shows the irradiated ones of the plasmonic structures 28 in a temporary state, illustrated with bubbles 48, prior to the formation of pores 50 in the membranes 46 of the target cells 12 once the temporary state has elapsed, such as shown in FIG. 3D. As can be appreciated, the presence of the pores 50 allows one or more of the exogenous biomolecules 26 nearby to be delivered into the target cell 12 via the pores 50.

It is noted that irradiating the plasmonic structures 28 with a laser beam having a wavelength $\lambda 2$ being tuned to the plasmonic resonance wavelength $\lambda p$ (i.e., when $\lambda 2 = \lambda p$) is generally to be avoided. Indeed, in this case, the plasmonic structures 28 may absorb too much of the optical power of the laser beam, which may inconveniently cause the plasmonic structures 28 to be heated passed a denaturation point, and then ultimately denatured in situ. Denaturation of the plasmonic structures 28 is preferably avoided because of the potentially toxic nature of some of the constituents of the plasmonic structures 28, which can lead to damaging of the surrounding cells. Accordingly, the wavelength $\lambda$ of the laser beam 42 is specifically chosen to be out of tune (i.e., off-resonance) with the plasmonic resonance wavelength $\lambda p$ of the plasmonic structures 28, to avoid excessive heating of the plasmonic structures 28 and thus damaging of surrounding cells.

The plasmonic structures 28 can be made of noble metals such as gold (Au), silver (Ag), aluminum (Al) copper (Cu), alloys thereof, or of any other suitable composition. As such, the plasmonic structures 28 need not be formed of noble metals. The plasmonic structures 28 can have any suitable geometry. For instance, the plasmonic structures 28 can have a spherical geometry, a rod-like geometry, a core shell geometry and the like. The plasmonic structures 28 can have a dimension which can range in the order of the nanometer, e.g., between 1 nm and 1000 nm. In this case, the plasmonic structures 28 can be referred to as plasmonic nanostructures (NSs) or nanoparticles (NPs). For instance, in one specific embodiment, the plasmonic structures are 100 nm gold nanostructures (AuNSs) or nanoparticles (AuNPs), i.e., the plasmonic structures are made of gold, have a spherical geometry with a diameter of 100 nm.

FIGS. 4A and 4B show target cells 12 and non-target cells 52. In the embodiment of FIG. 4A, the plasmonic structures 28 adjoin in a random manner the target cells 12 and onto the non-target cells 52. In some circumstances, it can be preferred to functionalize the plasmonic structures 28 so that they can target the target cells 12. Indeed, in the embodiment depicted in FIG. 4B, plasmonic structures 54 have been functionalized with a targeting molecule 56 adapted to target the membrane 46 of the target cells 12. For instance, the targeting molecule 56 can be an antibody molecule in some embodiments, whereas the targeting molecule 56 can be a functional group in some other embodiments. In this manner, the functionalized plasmonic structures 54 adjoin only the target cells 12, thus avoiding undesirable formation of pores in the non-target cells 52. In this case, the functionalized plasmonic structures 54 are in close proximity to the membranes of the target cells 12 due to the spacing distance of the targeting molecule 56. In some embodiments, the targeting molecule 56 can include antibodies, aptamers, peptides and/or any other suitable functionalization molecules.

In some embodiments, the functionalized plasmonic structures 54 can be provided in the form of stable bioconjugated AuNPs with biopolymers and antibodies (Abs) specifically targeting retinal pigment epithelium (RPE) cells (ARPE-19 cell line) in cell culture medium supplemented with serum proteins. Stable 100 nm AuNPs (Nanopartz) were bioconjugated sequentially with the biopolymer orthopyridyl disulfide-poly(ethylene glycol)-N-hydroxysuccinimide (OPSS-PEG-NHS) conjugated to monoclonal anti-CD44 Abs, followed by thiolated PEG chains (HS-PEG(5 kDa)). Data based on immunostaining, fluorescence and scanning electron microscopy, provide evidence for selective cell targeting with such stable Ab-AuNPs in cell culture medium containing serum proteins. Other types of functionalized plasmonic structures can be used as well.

In some embodiments, stable 100 nm AuNPs (purchased from Nanopartz) were bioconjugated sequentially with the biopolymer orthopyridyl disulfide-poly(ethylene glycol)-N-hydroxysuccinimide (OPSS-PEG-NHS) conjugated to monoclonal anti-$K_v$1.1 Abs, followed by thiolated PEG chains (HS-PEG(5 kDa)). In such embodiments, the mixture 16 was provided in the form of Abs-AuNPs obtained by briefly vortexing $K_v$1.1-AuNPs, centrifuging at 5000 rpm for 2 minutes, resuspending the centrifuged $K_v$1.1-AuNPs in 1% fluorescein isothiocyanate (FITC) diluted in 0.9% saline at a concentration of 100 μg/mL. In some other embodiments, the mixture 16 was provided in the form of bare AuNPs obtained by briefly vortexing bare AuNPs, centrifuging at 5000 rpm for 2 minutes and resuspending the centrifuged AuNPs in 1% FITC (0.9% saline) at a concentration of 100 μg/mL. However, other types of mixtures can be used.

In this specific case, the inventors have found that off-resonance laser irradiation in the NIR region of the electromagnetic spectrum using 100 nm AuNPs can minimize heat absorption in situ in target cells and thus can limit damaging of the surrounding non-target cells.

A ps laser beam (7.5 ps, 1064 nm, 76 MHz) was also used to optoporate ARPE-19 cells in the presence of bare AuNPs, propidium iodide (PI) and fluorescein isothiocyanate (FITC)-dextran (4 kDa). The energy output for optimal cell perforation was 300 mW with 0.4 mJ/cm$^2$. Under such fluence, PI and FITC-dextran penetrated into ~40% of laser-irradiated cells with low mortality rate (<5%, assessed with PI uptake). Interestingly, 300 mW was also one optimal power for cell optoporation with 45 fs pulses (800 nm, 60 mJ/cm$^2$, 500 Hz).

Table 1 shows examples of parameters (τ: time duration of laser pulses, λ: wavelength, Rr: repetition rate) of the irradiation subsystem which have been used in in vitro experiments.

|  | Example 1<br>τ = 45 fs<br>λ = 800 nm<br>Rr = 1 kHz | Example 2<br>τ = 100 fs<br>λ = 800 nm<br>Rr = 80 MHz | Example 3<br>τ 7.5 ps<br>λ = 1064 nm<br>Rr = 76 MHz |
|---|---|---|---|
| Optimal fluence (mJ/cm$^2$) | 60 | 0.5 | 0.4 |
| Spot size (μm) | 680 | 1 | 30 |
| Scanning velocity (mm/s) | 3.5 | 0.1 | 0.5 |
| Perforation efficiency (%) | 70 | 80 | 40 |

The parameters presented in Table 1 have been used for in vitro delivering of exogenous biomolecules into target retinal pigment epithelium cells (RPE, CD44+ ARPE-19 cell line as a model). However, it is believed that such parameters, or any other suitable parameters, could be used in in vivo embodiments. It was found preferred to limit the fluence of the femtosecond laser beam 142 so that a small amount of optical power be provided to the plasmonic structures, which can in turn limit modifications of the plasmonic structures and limit damaging of the surrounding non target cells.

In some examples, it may be convenient to irradiate the region of the eye with a pulsed laser beam having pulses of different shapes. As such, the pulsed laser beam can be optically processed to perform pulse shaping techniques in which the shape, and/or the duration of the pulses are manipulated. In such examples, the pulsed laser beam can include a first pulse having a first time duration followed by a second pulse having a second time duration different from the first time duration. For instance, the first time duration of the first pulse can be of 40 fs whereas the second time duration of the second pulse can be 500 fs.

In some other examples, the pulsed laser beam can include pulses of different wavelengths. In these examples, the pulsed laser beam can include a first pulse having a first wavelength followed by a second pulse having a second wavelength different from the first wavelength. For instance, the first wavelength of the first pulse can be 800 nm whereas the second wavelength of the second pulse can be 1000 nm.

In still other examples, the pulsed laser beam can include pulses of different fluences. In these examples, the pulsed laser beam can include a first pulse having a first fluence followed by a second pulse having a second fluence different from the first fluence. For instance, the first fluence of the first pulse can be 10 mJ/cm$^2$ nm whereas the second fluence of the second pulse can be 100 mJ/cm$^2$.

In alternate examples, the pulsed laser beam can include pulses delayed from one another. In such examples, the pulsed laser beam can have a first pulse being emitted at moment in time $t_0$ followed by a second pulse having a specific time delay $\Delta T$ with respect to the first pulse. For instance, the first pulse can be emitted at moment in time $t_0$ whereas the second pulse can be emitted at time $t_0+\Delta T$. In some cases, the time delay $\Delta T$ can be 1 ps.

As can be understood, in one specific example, the pulsed laser beam can have a first pulse having a first wavelength and a first time duration followed by a second pulse having a second wavelength and a second time duration and being delayed by a time delay $\Delta T$ with respect to the first pulse. As can be understood, the region of the eye can be repeatedly irradiated with the first and second pulses for a given amount of time.

The parameters presented in Table 1 were adapted to perform optoporation (perforation with light) of the target cells of the rodent eye 114. 100 fs laser pulses (with powers from 120 to 350 mW) were used in the presence of injected FITC-dextran (2 MDa) and K$_V$1.1-AuNPs targeting retinal ganglions cells (RGCs). The cell optoporation with FITC-dextran (2 MDa) indicate that smaller biomolecules such as siRNA or some drugs should be able to enter target laser-irradiated cells.

Additional Experiment—the Rodent Eye

FIG. 5 shows an example of a system 100 for delivering biomolecules into a target cell of a rodent eye. As depicted, the system 100 has a mixture 116, an irradiation subsystem 120 and an imaging subsystem 122.

In this specific example, manual injection of the mixture 116 was preferred over the robotized injection subsystem 18 described with reference to FIG. 1. Accordingly, for intraocular injections, the rodents were anaesthetized using a ketamize/xylazine mix (ketamine: 90 mg/kg, xylazine: 10 mg/kg). Then, 5 µL of the mixture 116 were manually injected into the vitreous chamber of the rodent eye 114 using a syringe (e.g., a Hamilton syringe) adapted with a glass-pulled needle. For subretinal injections, it was preferred to anesthetize the rodents using the ketamize/xylazine mix. Then, a paracentesis was made in the superior cornea with a 30½-gauge needle, allowing penetration of a 33-gauge unbeveled needle mounted on a syringe (e.g., Hamilton) to inject 3 µL of Ab-AuNPs with 1% fluorescein isothiocyanate FITC (0.9% saline) subretinally. The injected area can be visualized by FITC (fluorescence imaging with the green channel).

As depicted, the irradiation subsystem 120 which includes a laser source 160 and beam redirecting and formatting optics 162. The laser source 160 is provided in the form of a Ti-Sapphire femtosecond laser that can irradiate a laser beam 164 towards the beam redirecting and formatting optics 162. As can be understood, the beam redirecting and formatting optics 162 are used to redirect and format the laser beam 164 exiting the laser source 160 before the formatted and redirected laser beam 142 reaches the rodent eye 114.

The beam redirecting and formatting optics 162 can vary from one embodiment to another. However, in this specific example, the beam redirecting and formatting optics 162 includes an automated dispersion compensation subsystem 166 (Mai Tai® DeepSee™) to compensate the dispersion of the laser beam 164. As depicted, the beam redirecting and formatting optics 162 includes also other optical components such as half wave plates (HWPs) 168, beam splitters (BSs) 170, a shutter 172, a glass substrate 174, reflective surfaces 176, a telescope 178 including a first lens 180 and a second lens 182 to contract or expand a mode field diameter of the laser beam 164, and a periscope 184.

Also in this example, the imaging subsystem 120 is used to image the rodent eye 114 during the injection and/or during the irradiation of a region of the rodent eye 114. An example of such an imaging subsystem includes Heidelberg Spectralis HRA ophthalmoscope for fundus visualization. Other ophthalmoscopes can be used as well.

After injection of AuNPs in the region of the rodent eye 114, the region of the rodent eye 114 has been irradiated with a femtosecond laser beam 142 having a wavelength of 800 nm. The retinal surface of the rodent eye 114 was studied to estimate the spot size and fluence requirements. The spot size has been estimated at the retinal (70-75 µm) and choroidal surfaces (50 µm). Then, the strong optical aberrations originated on the cornea-air interface were mostly reduced by placing a concave lens in contact with the corneal surface of the rodent eye 114, thereby cancelling the optical power of that interface. In this example, a 4x objective was placed for focusing the femtosecond laser beam 142 on the retina.

By correcting the optical aberrations of the rodent eye 114, the femtosecond laser beam 142 was focused onto the retina of the rodent eye 114 to form pores locally and selectively. To enhance the ocular fundus imaging quality using the imaging subsystem 122, and to better focus on the retina of the rodent eye 114, it was found useful to provide a plano-concave lens 186 to the rodent eye 114, as best shown in FIG. 6. As it can be seen, the femtosecond laser beam 142 was focused on the retina of the rodent eye 114 using an objective 188, the plano-concave lens 186 and an optically transparent tear gel 190. In other examples, contact lenses can be applied over the eye to perform the focusing function of the plano-concave lens 186.

Figure 7B:
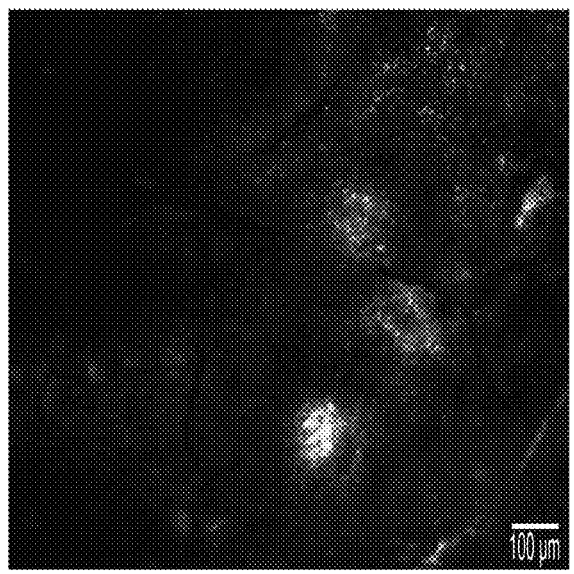
FIG. 7B is a confocal microscopy image of target cells of the rodent eye of FIG. 7A, taken in vivo, in the presence of gold nanoparticles (AuNPs) functionalized with $K_V1.1$ antibodies ($K_V1.1$-AuNPs) and of FITC-dextran (green, opto-poration dye), irradiated for 15 seconds by a pulsed laser beam having an optical power of 350 mW.
Figure 7C:
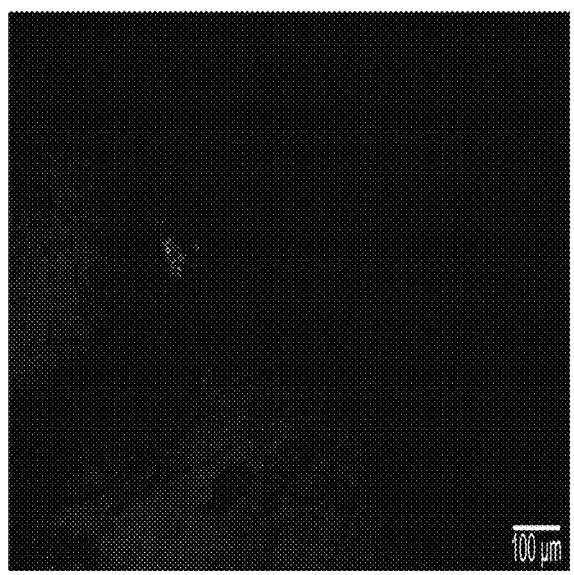
FIG. 7C is a confocal microscopy image of target cells of the rodent eye of FIG. 7A, taken in vivo, in the presence of $K_V1.1$-AuNPs and of Cy3-siRNA (red, fluorescently labeled siRNA), irradiated for 15 seconds by a pulsed laser beam having an optical power of 350 mW.
Figure 7D:
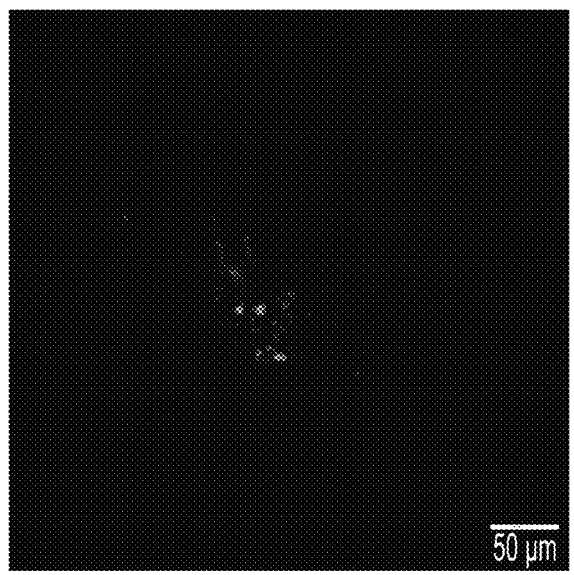
FIG. 7D are confocal microscopy images of target cells of the rodent eye of FIG. 7A, taken in vivo, in the presence of $K_V1.1$-AuNPs, and of Cy3-siRNA, irradiated for 15 seconds by a pulsed laser beam having an optical power of 120 mW.

The method described herein can be performed in vivo, with satisfactory results. More specifically, the method was used to, in vivo, form pores in target cells of a rodent eye using a laser beam and plasmonic structures. In this embodiment, the plasmonic structures were gold nanoparticles (AuNPs) functionalized with K$_V$1.1 antibodies (referred to as K$_V$1.1-AuNPs) targeting RGCs. For instance, example of results obtained on a rodent eye are presented in FIGS. 7A-D. More specifically, FIG. 7A is a confocal microscopy image showing an ocular fundus ophthalmoscope visualization of a rodent eye taken in vivo, and FIGS. 7B-D are confocal microscopy images of target cells of the rodent eye in the presence of K$_V$1.1-AuNPs. In the case of FIG. 7B, FITC-dextran (green, optoporation dye) was used whereas Cy3-siRNA (red, fluorescently labeled siRNA) was used in the case of FIGS. 7C-D, as they were irradiated for 15 seconds by the pulsed laser beam. In FIG. 7B, the pulsed laser beam had pulses with a time duration of 100 fs, a wavelength of 800 nm, a repetition rate of 80 MHz and an optical power of 350 mW; in FIG. 7C, the pulsed laser beam had pulses with a time duration of 100 fs, a wavelength of 800 nm, a repetition rate of 80 MHz and an optical power of 350 mW; and in FIG. 7D, the pulsed laser beam had pulses with a time duration of 100 fs, a wavelength of 800 nm, a repetition rate of 80 MHz and an optical power of 120 mW.

The methods described herein can be useful in delivering exogenous biomolecules to the eye while avoiding viral approaches which may be less desirable. The methods can allow for selective delivery to targeted cells using irradiation subsystems which can be available in ophthalmology practices. In addition, the methods described herein can provide a unique double selectivity: Ab-AuNPs target cell-specific surface biomarkers and a high spatial precision laser beam ensure delivery exclusively to the target cells, thus limiting off-target side effects.

The impact of the methods described herein on drug discovery for retinal degenerative and other diseases may be several-fold. For instance, the methods may reduce research and development costs and time to market by providing an in vivo mid-throughput screening tool for compounds in pre-clinical studies. Also, the methods may open novel therapeutic and research avenues by providing a powerful integrated tool for delivery of therapeutic exogenous biomolecules (e.g., therapeutic genes, silencing RNAs, small molecules, drugs) to the human eye. Further, the methods can have the potential to increase the efficacy of existing drugs, reduce their doses to reach effective concentrations and thus reduce their toxicity and off-target effects.

As can be understood, the examples described above and illustrated are intended to be exemplary only. For instance, the injection of the mixture can include a first step of injecting, into the region of the eye, a solution having a solvent in which are dissolved the exogenous biomolecules, and a second step of injecting, into the region of the eye, a colloidal suspension having a substance in which are suspended the plasmonic structures. The first and second steps of injecting can be performed sequentially. For instance, the solution can be injected prior to the colloidal suspension, or vice-versa. Otherwise, the exogenous biomolecules and the plasmonic structures can be injected simultaneously in a single injection step. As it will be understood, the exogenous biomolecules can be omitted in the mixture injected into the region of the eye, leaving only the plasmonic structures suspended into a colloidal suspension. In this specific case, the method can be used for forming one or more pores into a membrane of a target cell of the eye, without necessarily delivering one or more exogenous biomolecules thereinside. In other words, the exogenous biomolecules can be optional. As may be appreciated by the person skilled in the art, the plasmonic structures are said to have a plasmonic resonance wavelength $\lambda p$. However, the plasmonic resonance wavelength $\lambda p$ can be characterized equivalently as having a plasmonic resonance frequency $fp$, which can be determined from the plasmonic resonance wavelength $\lambda p$ using the speed of light c and the refractive index n in which the laser beam is propagated ($c=n*\lambda p*fp$). Although the methods described herein has been described with reference to the human eye and the rodent eye, the methods could alternately be used with any suitable eyes such as mammal eyes, reptile eyes, fish eyes (e.g., a Zebra fish eye). The scope is indicated by the appended claims.

What is claimed is:

1. A method for delivering exogenous biomolecules into an eye, the method comprising the steps of:
    injecting, into a region of the eye, a mixture having a plurality of exogenous biomolecules and a plurality of plasmonic structures, the plasmonic structures having a plasmonic resonance wavelength, the plasmonic structures adjoining membranes of target cells in said region due to said injecting, said injecting including a step of injecting, into the region of the eye, a solution having a solvent in which are dissolved the plurality of exogenous biomolecules, and another step of injecting, into the region of the eye, a colloidal suspension having a substance in which are suspended the plurality of plasmonic structures, the steps of injecting of injecting being performed sequentially; and
    irradiating said region of said eye with a laser beam having a wavelength being offset to said plasmonic resonance wavelength, said irradiating causing the plasmonic structures to form pores in said membranes of said target cells, allowing at least some of the exogenous biomolecules to be delivered into the target cells via said pores.

2. The method of claim 1 wherein said region is a retinal region of said eye.

3. The method of claim 2 wherein said injecting is provided in the form of one of the group consisting of: a subretinal injection and a intravitreal injection.

4. The method of claim 1 further comprising, prior to said irradiating, waiting a given period of time.

5. The method of claim 4 wherein said period of time is below 3 hours.

6. The method of claim 1 further comprising, prior to said injecting, functionalizing the plurality of plasmonic structures with a targeting molecule adapted to target said membrane of said target cell.

7. The method of claim 1 wherein said wavelength of said laser beam is within an optically transparent window of the eye.

8. The method of claim 7 wherein said optically transparent window is in the near-infrared region of the electromagnetic spectrum.

9. The method of claim 1 wherein the plasmonic structures are plasmonic nanostructures having a dimension ranging between 1 nm and 1000 nm.

10. The method of claim 1 wherein said plasmonic structures are made of gold.

11. The method of claim 1 wherein said plasmonic structures have a spherical geometry.

12. The method of claim 1 wherein said laser beam is a femtosecond laser beam with pulses having a time duration in the femtosecond range.

13. The method of claim 1 further comprising imaging said region of said eye while said irradiating.

14. A system for delivering exogenous biomolecules into an eye, the system comprising:
    a mixture having a plurality of exogenous biomolecules and a plurality of plasmonic structures, said mixture being injectable into a region of said eye in a manner resulting in the plasmonic structures adjoining membranes of target cells of said eye, the plasmonic structures having a plasmonic resonance wavelength; and
    an irradiation subsystem configured for irradiating said region of said eye with a laser beam having a wavelength being offset to said plasmonic resonance wavelength, said irradiating causing the plasmonic structures to form pores in said membranes of said target cells, allowing at least some of the exogenous biomolecules to be delivered into the target cells via said pores, wherein said laser beam is a femtosecond laser beam with pulses having a time duration in the femtosecond range.

15. The system of claim 14 wherein said plasmonic structures are gold nanoparticles.

16. The system of claim 14 further comprising a lens optically coupled to an external surface of the eye for correcting optical aberrations of the eye.

17. The system of claim 4 further comprising an imaging subsystem configured for imaging said region of said eye.

18. A method for delivering exogenous biomolecules into an eye, the method comprising the steps of:
- injecting, into a region of the eye, a mixture having a plurality of exogenous biomolecules and a plurality of plasmonic structures, the plasmonic structures having a plasmonic resonance wavelength, the plasmonic structures adjoining membranes of target cells in said region due to said injecting; and
- irradiating said region of said eye with a laser beam having a wavelength being offset to said plasmonic resonance wavelength, said irradiating causing the plasmonic structures to form pores in said membranes of said target cells, allowing at least some of the exogenous biomolecules to be delivered into the target cells via said pores, wherein said laser beam is a femtosecond laser beam with pulses having a time duration in the femtosecond range.

19. The system of claim 17, wherein said imaging subsystem is provided in the form of an ophthalmoscope.

\* \* \* \* \*